United States Patent
Boyd et al.

(10) Patent No.: US 6,872,314 B2
(45) Date of Patent: Mar. 29, 2005

(54) DEWATERING PROCESS

(75) Inventors: Brendan William Boyd, Johnson City, TN (US); Bhaskar Krishna Arumugam, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 32 days.

(21) Appl. No.: 10/651,819

(22) Filed: Aug. 29, 2003

(65) Prior Publication Data

US 2005/0045560 A1 Mar. 3, 2005

(51) Int. Cl.$^7$ .............................................. B01D 15/08
(52) U.S. Cl. ..................... 210/635; 210/659; 210/198.2; 210/672
(58) Field of Search .............................. 210/635, 656, 210/659, 198.2, 662, 672; 127/46.1, 46.2, 46.3

(56) References Cited

U.S. PATENT DOCUMENTS

| | | |
|---|---|---|
| 2,462,251 A | 2/1949 | Bassford, Jr. et al. |
| 2,491,065 A | 12/1949 | van Eekelen et al. |
| 2,956,070 A | 10/1960 | Jennings et al. |
| 4,182,633 A | 1/1980 | Ishikawa et al. |
| 4,302,222 A | 11/1981 | Miller et al. |
| 4,323,702 A | 4/1982 | Kawabata et al. |
| 4,333,740 A | 6/1982 | Priegnitz |
| 4,483,980 A | 11/1984 | Neuzil et al. |
| 4,522,726 A | 6/1985 | Berry et al. |
| 4,720,579 A | 1/1988 | Kulprathipanja |
| 4,764,276 A | 8/1988 | Berry et al. |
| 4,808,317 A | 2/1989 | Berry et al. |
| 4,851,573 A | 7/1989 | Kulprathipanja et al. |
| 4,851,574 A | 7/1989 | Kulprathipanja et al. |
| 4,923,616 A | 5/1990 | Hirata et al. |
| 4,970,002 A | 11/1990 | Ando et al. |
| 5,032,686 A | 7/1991 | Duflot et al. |
| 5,064,539 A | 11/1991 | Tanimura et al. |
| 5,071,560 A | 12/1991 | McCulloch et al. |
| 5,114,590 A | 5/1992 | Hotier et al. |
| 5,382,681 A | 1/1995 | Derez et al. |
| 5,391,770 A | 2/1995 | Le Fur et al. |
| 5,405,992 A | 4/1995 | Funk et al. |
| 5,412,126 A | 5/1995 | King et al. |
| 5,637,734 A | 6/1997 | Honda et al. |
| 5,744,618 A | 4/1998 | Fechtel et al. |
| 5,744,634 A | 4/1998 | Veits |
| 5,817,238 A | 10/1998 | Makino et al. |
| 6,033,714 A | 3/2000 | Gugger et al. |
| 6,146,534 A | 11/2000 | Grendze et al. |
| 6,153,791 A | 11/2000 | Moore |
| 6,395,179 B1 | 5/2002 | Grendze et al. |
| 6,476,239 B1 | 11/2002 | Arumugam et al. |
| 6,518,454 B1 | 2/2003 | Arumugam et al. |
| 2002/0151726 A1 | 10/2002 | Arumugam et al. |

FOREIGN PATENT DOCUMENTS

| | | |
|---|---|---|
| DE | 199 38 980.2 A1 | 2/2001 |
| EP | 0 324 210 B1 | 7/1989 |
| EP | 0 671 405 A1 | 1/1995 |
| EP | 1 106 602 A1 | 6/2001 |
| EP | 1 176 131 A1 | 1/2002 |
| WO | WO 98/00839 A1 | 1/1998 |
| WO | WO 99/03853 A1 | 1/1999 |

OTHER PUBLICATIONS

Mazzotti et al. *Ind. Eng. Chem. Res.* 1997, 36, pp. 3163–3172.

White et al. "*Potential Application for Industrial Scale Chromatography*", presented at the 211$^{th}$ ACS Nat'l Meeting, New Orleans, LA., Mar. 27 and 28, 1996.

Carta et al. *Ind. Eng. Chem. Res.* 2002, 41, pp. 4722–4732.

Broughton, *Production–Scale Adsorptive Separations of Liquid Mixtures by Simulated Moving–Bed Technology*, Separation Science and Technology, 19 (11 & 12), 1984–85, pp. 723–736.

Navarro et al, *Continuous chromatographic separation process: simulated moving bed allowing simultaneous withdrawal of three fractions*, Journal of Chromatography A, 770 (1997) pp. 39–50.

Wankat, Phillip, *Rate–Controlled Separations*, Elsevier Applied Science, 1990, pp. 524–533.

Feng et al, *Studies of a Membrane Reactor: Esterification Faciliated by Pervaporation*, Chemical Engineering Science, vol. 51, No. 20, pp. 4673–4679.

Okamoto et al, *Pervaporation–Aided Esterification of Oleic Acid*, Journal of Chemical Engineering of Japan, vol. 26, No. 5, 1993, pp. 475–481.

Kwon et al, *Removal of Water Produced from Lipase–Catalyzed Esterification in Organic Solvent by Pervaporation*, Biotechnology and Bioengineering, vol. 46, 1995, pp. 393–395.

(Continued)

Primary Examiner—Ernest G. Therkorn
(74) Attorney, Agent, or Firm—Eric D. Middlemas; Bernard J. Graves, Jr.

(57) ABSTRACT

Disclosed is a process for dewatering an organic compound other than a carboxylic acid using a simulated moving bed (SMB) containing a solid with different absorptivities for water and the organic compound. The organic compound is fed into the SMB as an aqueous solution and desorbed with a desorbent other than water. The process is particularly useful for dewatering organic compounds produced by fermentation, biomass extraction, biocatalytic, and enzymatic processes.

21 Claims, No Drawings

OTHER PUBLICATIONS

Keurentjes et al, *The Esterification of Tartaric Acid with Ethanol:Kinetics and Shifting the Equilibrium by Means of Pervaporation*, Chemical Engineering Science, vol. 49, No. 24A, 1994, pp. 4681–4689.

Xiuyuan et al, *Modified Aromatic Polymide Membrane Preparation and Pervaportion Results for Esterification System*, Water Treatment, 10, 1995, pp. 115–120.

Kawase et al, *Increased Esterification Conversion by Application of the Simulated Moving–Bed Reactor*, Chemical Engineering Science, vol. 51, No. 11, 1996, pp. 2971–2976.

Perrin et al, *The Use of SMB for the Manufacture of Enantiopure Drug Substances: From Principle to cGMP Compliance*, Chiral Separation Techniques: A Practical Approach, 2001, pp. 253–285.

Derwent Abstract JP 73015931, Oct. 5, 1970, Takeda Chem. Ind. Ltd.

DEWATERING PROCESS

FIELD OF THE INVENTION

This invention pertains to a process for dewatering organic compounds. More particularly, this invention pertains to a process for separating water from an organic compound using a simulated moving bed (SMB).

BACKGROUND OF THE INVENTION

The separation of water from organic compounds has been a ongoing challenge for the chemical industry. Typically, techniques such as distillation, decantation, extraction, pervaporation, and chromatography have been employed. These methods, however, often are energy intensive, expensive to operate, and may not be practical or economical for the recovery and purification of materials from dilute aqueous solutions. For example, chemical products such as glucose, which is isolated from biomass, and fermentation products such as lactic acid, phenylalanine, citric acid, L-amino acids, succinic acid, and ascorbic acid, typically must be separated, recovered, and purified from dilute aqueous solutions or fermentation broths. The recovery costs for such fermentation processes are often the major factor which determines their commercial success. The presence of water in chemical products also often complicates purification methods such as crystallization, waste disposal methods, such as incineration, and the recovery and recycling of solvents.

Adsorption from the liquid phase has been disclosed as a method to recover and purify carboxylic acids from dilute aqueous process streams. A variety of carboxylic acids and adsorbents have been reported. For example, European Patent No. 0 324 210 B1 and U.S. Pat. Nos. 4,323,702; 4,720,579; 4,851,573; 4,851,574; and 6,153,791 disclose methods of recovering carboxylic acids or carboxylate salts by adsorption with a polymeric adsorbent resins. Typical resins that have been used as adsorbents are neutral, cross-linked polystyrene polymers, nonionic hydrophobic polyacrylic ester polymers, weakly basic anion exchange resins possessing tertiary amine or pyridine functional groups, and strongly basic anion exchange resins possessing quaternary amine functional groups. The carboxylic acid, generally, is adsorbed on the polymeric adsorbent and then desorbed. The pH of the feed stream may be adjusted to increase the selectivity of the adsorption process. The most common desorbent is water, although solvents such as acetone, ketones, esters, methanol, and ethanol have been used. U.S. Pat. No. 6,153,791, for example, describes a process for the purification of 2-keto-L-gulonic acid by a continuous chromatographic process using a weakly basic ion exchange resin. The adsorbed 2-keto-L-gulonic acid may be desorbed with water or a lower alcohol, such as methanol or ethanol. Similarly, U.S. Pat. No. 6,146,534 discloses processes utilizing thermally-managed chromatography over solid adsorbents for treating aqueous acids to dewater and recover the acids in an organic solvent such as an alcohol. In another example, U.S. Pat. No. 5,071,560 describes a process for the liquid phase adsorptive separation of phenylalanine from a fermentation broth containing phenylalanine salts, carbohydrates, amino acids and organic acids. The feed is contacted, at a pH of 4.5–6.5, with a hydrophobic polar, porous synthetic adsorbent, such as Amberlite XAD-7, whose functional groups have a dipole moment of 1.6–2.0, to selectively adsorb the phenylalanine onto said adsorbent to the substantial exclusion of the other feed components and recovering phenylalanine by desorbing with water, an alcohol, a ketone or an ester.

Adsorption has been used also to remove the water produced during esterification reactions and thereby shift the reaction equilibrium toward esterification. U.S. Pat. No. 5,405,992 discloses a process for the continuous esterification of at least one alcohol and at least one carboxylic acid to form at least one ester and water with the concurrent separation of the esterification products. The process uses a simulated moving bed in which the adsorbent acts both as a catalyst for esterification and as an adsorbent for at least one of the products. In addition, U.S. Pat. Nos. 6,518,454 and 6,476,239 describe processes for the preparation of esters and for the preparation of ascorbic acid, respectively, in a simulated moving bed reactor.

Also disclosed are adsorptive methods of purifying and recovering glucose and ethanol. For example, a process for the recovery of glucose from an aqueous mixture of glucose and polysaccharides is described in U.S. Pat. No. 4,483,980 using countercurrent and co-current simulated moving beds. The mixture is contacted with an X zeolite containing potassium cations at exchangeable cationic sites and selectively adsorbing glucose in the zeolite. The polysaccharides are removed from the zeolite and the adsorbed glucose recovered by means of a desorbent liquid. U.S. Pat. No. 4,333,740 discloses an absorptive process for separating water from a feed mixture comprising ethanol and water, which comprises contacting the feed mixture with an adsorbent comprising corn meal, selectively adsorbing substantially all of the water to be separated to the substantial exclusion of the ethanol, and thereafter recovering high purity ethanol. The process employs a countercurrent moving bed or simulated moving bed countercurrent flow system.

The known methods for dewatering organic compounds are limited primarily to organic acids and typically utilize a strong charge—charge interaction between the acid and adsorbent, such as ion-exclusion, as the primary separation mechanism. Because such charge—charge interactions are weak or non-existent for neutral organic compounds, these methods are not, in general, applicable for dewatering organic compounds without carboxyl substituents. A dewatering process is needed, therefore, that may be used for broad range organic compounds, avoids the limitations discussed above, and may be operated inexpensively on a commercial scale. Such a dewatering process would find commerical application within the chemical and pharmaceutical industries where there is strong interest in the development of water-based fermentation and enzymatic processes.

SUMMARY OF THE INVENTION

We have unexpectedly discovered that organic compounds other than carboxylic acids may be dewatered efficiently and inexpensively through adsorption using a simulated moving bed. In a general embodiment, our invention provides a process for separating water from an organic compound comprising:

I. feeding (i) an aqueous solution comprising at least one organic compound which is not a carboxylic acid and (ii) a desorbent, other than water, having at least a partial solubility in water to a simulated moving bed comprising at least one solid having different adsorptivities for said organic compound and water; and II. removing from said simulated moving bed (i) a first liquid stream comprising said organic compound and said desorbent and (ii) a second liquid stream comprising water from said aqueous solution of step I.

Our process separates water from an organic compound and simultaneously replaces water with the desorbent, thereby effecting a solvent exchange with the water originally present. Our invention is applicable to a broad range of organic compounds such as, for example, alcohols, polyhydroxy compounds, esters, carbohydrates, aldehydes, sulfones, thioketones, oximes, ketones, nitrites, amides, lactones, lactams, phenols, amines, ethers, and heterocyclic compounds, and may use a variety of desorbents such as, for example, alcohols, diols, esters, nitrites, ketones, and ethers. Our invention uses a simulated moving bed comprising a solid with different adsorptivities for water and the organic compound and provides a general and inexpensive way to dewater organic compounds that avoids the difficulties of heat sensitivity and formation of water azeotropes.

Another embodiment of the present invention is a process for separating water from an organic compound comprising:

I. feeding (i) an aqueous solution comprising at least one organic compound selected from alcohols, ethers, ketones, polyhydroxy compounds, and esters; and (ii) at least one desorbent selected from alcohols, esters, ketones, and ethers, having at least a partial solubility in water to a simulated moving bed comprising at least one solid having different adsorptivities for said organic compound and water; and II. removing from said simulated moving bed (i) a first liquid stream comprising said organic compound and said desorbent and (ii) a second liquid stream comprising water from said aqueous solution of step I.

Our invention is useful for dewatering low boiling esters such as, for example, esters of acetic, butyric, and propionic acids which form constant boiling azeotropes with water and which require multiple processing steps to obtain free from water. The invention is also useful for dewatering heat sensitive compounds such as sugars, such as, for example, glucose, fructose, sucrose, and maltose; and high boiling polyhydroxy compounds such as, for example, ethylene glycol, 1,2-propanediol, 1,3-propanediol, 1,2-butanediol, 1,3-butanediol, 1,4-butanediol, pentaerythritol, and trimethylolpropane, which are troublesome and expensive to dewater by conventional methods.

DETAILED DESCRIPTION

The present invention provides a dewatering process that is applicable to a broad scope of non-acidic organic compounds and which may be operated inexpensively on a commercial scale. Thus, our invention provides a process for separating water from an organic compound comprising:

I. feeding (i) an aqueous solution comprising at least one organic compound which is not a carboxylic acid and (ii) a desorbent, other than water, having at least a partial solubility in water to a simulated moving bed comprising at least one solid having different adsorptivities for said organic compound and water; and II. removing from said simulated moving bed (i) a first liquid stream comprising said organic compound and said desorbent and (ii) a second liquid stream comprising water from said aqueous solution of step I.

Although the process of the present invention may be used to dewater carboxylic acids, our process is for separating water from organic compounds which are not carboxylic acids. The present invention utilizes a simulated moving bed to accomplish the dewatering process which provides a low-temperature, continuous process for the separation of water that avoids thermal degradation of heat sensitive organic compounds, such as carbohydrates, and is less energy intensive than traditional separation methods such as distillation or crystallization. The instant invention, thus, is useful for the separation of chemicals from the dilute, aqueous process streams typically produced by fermentation and biocatalytic processes.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint (s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "$C_1$ to $C_5$ hydrocarbons", is intended to specifically include and disclose $C_1$ and $C_5$ hydrocarbons as well as $C_2$, $C_3$, and $C_4$ hydrocarbons.

Notwithstanding that the numerical ranges and parameters setting forth the broad scope of the invention are approximations, the numerical values set forth in the specific examples are reported as precisely as possible. Any numerical value, however, inherently contain certains errors necessarily resulting from the standard deviation found in its testing measurements.

Our dewatering process may be carried using one or more fixed chromatographic beds containing the adsorbent solid which may be alternatively contacted with the feed mixture and desorbent materials. In the simplest embodiment of the invention, the adsorbent solid is employed in the form of a single static bed in which case the process is only semi-continuous. In another embodiment, a set of two or more static beds may be employed where the beds are connected by appropriate piping and valving such that the feed mixture may be passed through one or more adsorbent beds while the desorbent materials may be passed through one or more of the other beds in the set. The flow of feed mixture and desorbent materials may be either up or down through the desorbent. Any of the conventional apparatus employed in static bed fluid-solid contacting may be used.

Moving bed or simulated moving bed (abbreviated hereinafter as "SMB") systems, however, have a much greater separation efficiency than fixed adsorbent bed systems and are therefore preferred for use in the process of the present invention. In moving bed or simulated moving bed processes, the adsorption and desorption operations are continuously taking place which allows both continuous production of an extract (i.e., the material most strongly adsorbed by the adsorbent) and a raffinate (the material less strongly adsorbed by the adsorbent) stream and the continual use of feed and desorbent streams. One embodiment of this process utilizes what is known in the art as the simulated moving bed countercurrent flow system. In such a system, the progressive movement of multiple liquid access points down an adsorbent chamber simulates the upward movement of adsorbent contained in the chamber. Only four of the access lines are active at any one time: the feed input stream, desorbent inlet stream, raffinate outlet stream, and extract outlet stream access lines. Coincidental with this simulated upward movement of the solid absorbent is the movement of the liquid occupying the void volume of the packed bed of adsorbent. To maintain countercurrent contact, a liquid flow down the adsorbent chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divide the adsorbent chamber into separate zones, each of which has a different function. It is generally necessary that three separate operational zones be present in order for the process to take place although, for economical operation, it is generally preferable that a fourth zone be used. There is a net positive fluid flow through all portions of the column in the same direction, although the composition and rate of the fluid will, of course, vary from point to point.

The simulated moving bed utilized in the present invention is a known apparatus and comprises one or more chambers or columns, each of which contains a solid or mixture of solids or adsorbents. The SMB may consist of one or more sections comprising a plurality of zones and, typically, is equipped with a plurality of inlet and outlet ports. In the present invention, the SMB typically has 4–20 sections. The SMB is packed with a solid or mixture of solids having different adsorptivities for the organic compound and water and, thus, is effective separating water from the organic compound by selective adsorption. For example, the SMB may be equipped with two inlet streams: the first, an aqueous solution comprising at least one organic compound which is not a carboxylic acid and, the second, a desorbent, other than water, having at least a partial solubility in water. The SMB is equipped with a rotary valve or a plurality of valves arranged in a manner such that any feed stream may be introduced to any section or zone and any outlet or effluent stream may be withdrawn from any section or zone. During the operation of the SMB, the sections to which the feed streams are fed and from which the outlet streams are withdrawn are periodically moved. To achieve separation of reaction products, the locations of the inlet and outlet streams are moved intermittently in the direction of liquid flow. The intermittent port movement in the direction of liquid flow simulates the counter-current movement of the bed or beds of the solid(s), e.g., the solid adsorbent. Different equipment and operational strategies have been used to simulate the counter-current movement of the solid with respect to the liquid. See, for example, D. B. Broughton, *Production-Scale adsorptive separations of liquid mixtures by simulated moving bed technology*, Separation Science and Technology, 19, 723 (1984–1985) and U.S. Pat. Nos. 4,764,276; 4,923,616; 4,182,633; and 5,064,539. The process of the present invention may be carried out with all such variations of the SMB concept. A detailed description of the basic SMB process is provided by Wankat, *Rate-Controlled Separations*, Elsevier Applied Science, 1990, page 524.

The feed to our process is typically an aqueous solution of an organic compound, (also referred to herein as the "solute"). The term "aqueous solution", as used herein, is intended to mean a solution of an organic compound or mixture of organic compounds in water in which the weight % (based on the total weight of the solution and abbreviated hereinafter as "wt %") of water exceeds that of the organic compound, or solutions containing water dissolved in the organic compound in which the wt % of the organic compound exceeds that of water. Although the concentration of water is not critical, examples of aqueous solutions which may be used in the present invention are 50 wt % ethylene glycol, 50 wt % water; 75 wt % glucose, 25 wt % water; 5 wt % 1,3-propylene glycol, 95 wt % water; 10 wt % ethylene glycol, 20 wt % methyl acetate, 10 wt % ethyl acetate, 50 wt % water. Typically, the water concentration of the aqueous solutions in accordance with the present invention are from about 0.5 wt % to about 99.5 wt %. Other examples of water concentrations are from about 1 wt % to about 99 wt %, about 5 wt % to about 95 wt %, and from about 10 wt % to about 95 wt %.

The process of the invention dewaters an organic compound. As used herein, the term "dewater" is used interchangeably with and intended to be synonymous with removing and/or replacing at least a portion of the water present in the aqueous solution of the organic compound with an organic solvent. Thus, in as much as the water present with the organic compound may be considered as a solvent for the organic compound, our process accomplishes a solvent exchange by replacing at least a portion of the water originally present with an organic solvent.

The aqueous solution may comprise at least one organic compound which is not a carboxylic acid. The term "carboxylic acid", as used herein, means an organic compound bearing one or more carboxyl groups in the hydrogen form or as a metal or amine salt. Carboxylic acids are intended to include amino acids, proteins, and aliphatic, cycloaliphatic, aromatic, aralkyl, and heterocyclic carboxylic acids. According to the present invention, carboxylic acid esters are not intended to be included as carboxylic acids. The organic compound should be at least partially miscible or soluble in water such that under separation conditions of temperature, concentration, and pressure, only one liquid phase is present in the separation apparatus. The terms "miscible" or "soluble", as used herein in reference to the organic compounds, desorbents, and solvents, means that the solute dissolves uniformly in water. By "partially miscible" or "partially soluble", it is meant that the solute (e.g., the organic compound or desorbent) will dissolve in water to form at least a 1 wt % solution. Typically, the organic compound will contain from 1 to about 20 carbon atoms and, more typically, from 1 to about 10 carbon atoms. Examples of organic compounds which may be dewatered with the process of the invention include alcohols, sugars, polyhydroxy compounds, monosaccharides, disaccharides, oligosaccharides, polysaccharides, esters, carbohydrates, aldehydes, sulfones, thioketones, oximes, ketones, nitriles, amides, lactones, lactams, phenols, amines, ethers, and $C_4$ to $C_{10}$ heterocyclic compounds containing from 1 to 3 heteroatoms. Further non-limiting examples of organic compounds which may be dewatered include glucose, fructose, xylose, maltose, butanol, pentanol, xylitol, 1,2-propandiol, ethylene glycol, ethanol, propanol, hexanol, hexanediol, sorbitol, ethyl amine, butyl amine, tert-butyl amine, acetone, butanone, cyclobutanone, 1,4-cyclohexanedimethanol, cyclohexanol, pentaerythritol, trimethylol propane, butyraldehyde, 2-ethylhexanol, 2-ethylhexaldehyde, cyclopropanecarboxaldehyde, cyclopropanecarboxamide, sucrose, butyronitrile, isobutyronitrile, caprolactam, methyl isopropylketone, and methylpropylketone.

The aqueous solution of the organic compound may comprise one or more solvents in addition to water. The solvent may be an alcohol, e.g., a straight- or branched-chain, unsubstituted or substituted alcohol containing up to about 8 carbon atoms. As noted hereinabove, the aqueous solution may contain a wide range of concentrations of the organic compound(s) and any solvents that may be present. Examples of aqueous solutions that may be used in our process are dilute aqueous solutions of the organic compound (for example, 95 wt % water and 5 wt % organic compound), concentrated aqueous solutions of organic compounds (for example, an aqueous solution containing 20 wt % or greater of the organic compound), and miscible solutions of the organic compound and water in a solvent other than water (for example, an acetone solution containing 70 wt % acetone, 20 wt % organic compound, and 10 wt % water). If a solvent is present in addition to water, it should be soluble or miscible in water such that only one liquid phase is present. Examples of solvents which may be used are alcohols, such as methanol, ethanol, propanol, isopropanol, and butanol; diols, such as ethylene glycol, 1,3-propanediol, 1,2-propanediol, and 1,4-butanediol; esters, such as methyl acetate, ethyl acetate, propyl acetate, and methyl propionate; nitriles, such as acetonitrile; ketones, such as acetone, methyl ethyl ketone, and diethyl ketone; and aliphatic and cyclic ethers, such as dimethyl ether, tetrahydrofuran, and dioxane.

The process of our invention is particularly useful for the purification and separation of water from organic compounds produced by fermentation, biocatalytic, or enzymatic processes in which the desired organic compound is produced in a dilute aqueous solutions. For example, fermentation broths are obtained by the cultivation of one or more microorganisms that are designed to produce the desired organic compound. In addition to the desired organic compound and water, fermentation broths typically contain other dissolved materials such as the nutrients required by the microorganism(s) being employed, for example, amino acids, inorganic and/or organic salts, carbohydrates such as glucose; sorbose, mannose, disaccharides, and trisaccharides, depending upon the sugar feedstock to the fermenter, and various growth factors. The fermentation broth normally is filtered to remove biomass and other insoluble materials and may be treated with activated charcoal for color removal prior to being used in our novel dewatering process.

The dilute aqueous product solutions obtained from fermentation, enzymatic, and biocatalytic processes typically contain the desired organic compounds at a concentration of about 0.5 to 50 wt %, based on the total weight of the solution, more typically about 7 to 15 wt %, and water at a concentration of about 50 to 98 wt %, more typically about 75 to 95 wt %. The product solution may be fed directly to the simulated moving bed or may be further concentrated by conventional techniques such as evaporation and distillation before introduction into the SMB.

The simulated moving bed contains one or more solids having different adsorptivities for the organic compound and water. The terms "adsorption" or "adsorptivity", as used herein, are intended to have the commonly understood meanings by persons skilled in the art, i.e., the tendency or affinity of gases, liquids, or solutes to accumulate on the surface of a solid or adsorbent. Similarly, terms "solid", "adsorbent", and "solid adsorbent", as used herein in regards the adsorbent material contained within a SMB or other chromatographic system, are intended to be synonymous and are used interchangeably.

Because of these different adsorptivities, our process separates water and the organic by selective adsorption of either water or the organic compound by the adsorbent. The solid or mixture of solids used in the SMB are selected on the basis of the organic compound, the amount of water and solvents present, the desorbent, and the desired separation. The solid or mixture of solids is by necessity insoluble in the liquid streams employed in our process. If more than one adsorbent is used, the simulated moving bed unit may be packed with a uniform mixture of two (or three) solid materials or the solid materials may be packed in different segments. Examples of suitable adsorbents include activated carbon, molecular sieves, alumina, silica, silica-alumina, titania, polymeric resins containing one or more groups selected from sulfonate, hydroxy, amino, halogen, pyridyl, mono-substituted amino, disubstituted amino, acyl, acyloxy, keto, alkoxy, and polymeric resins containing immobilized silver or lead, commonly known as immobilized metal affinity columns (abbreviated herein as "IMAC"). Further examples of adsorbents are Amberlite® XAD-4, XAD-7, and XAD-8 resins, available from Rohm & Haas Co.

In another example, the adsorbent may be a sulfonated polymeric resin, such as an acidic ion exchange resin, e.g., a macroreticulated polymeric material derived from styrene or styrene and divinylbenzene containing pendant sulfonic acid groups. Examples of such acidic ion exchange resins include Amberlyst® 15, available from Rohm and Haas Company, Dowex® Monosphere 99 H, available from Dow Chemical Company, and Lewatit® M S100, SP112, K1221, and K2641, available from Bayer AG. Such acidic ion exchange resins have an affinity for water. The difference in the affinity of the acidic ion exchange resin for water and for an organic compounds, for example, glucose, can be utilized advantageously to effect a separation between water and glucose feed.

The present invention uses a desorbent, that is, a liquid or solvent capable of displacing a selectively adsorbed organic compound from the adsorbent. Because the process of the instant invention is a dewatering process, the desorbent may not be water but may contain from 0 to about 10 wt % of water. The desorbent should be at least partially miscible with water and the organic compound under SMB operating conditions of concentration, temperature, and pressure. Example ranges of water concentrations that may be present in the desorbent are from about 0.5 to about 10 wt %, about 1 to about 8 wt %, and about 3 to about 5 wt %. The desorbent may be a single solvent or a mixture of solvents. For example, the desorbent may comprise at least one solvent selected from alcohols, diols, esters, nitriles, ketones, and ethers. In one embodiment, the desorbent may be a straight- or branched-chain, unsubstituted or substituted alcohol, diol, ester, nitrile, ketone, or ether containing up to about 10 carbon atoms. Examples of desorbents include methanol, ethanol, propanol, isopropanol, and butanol; diols, such as ethylene glycol, 1,3-propanediol, 1,2-propanediol, and 1,4-butanediol; nitriles, such as acetonitrile and butyronitrile; ketones, such as acetone, methyl ethyl ketone, and diethyl ketone; esters, such as methyl acetate, ethyl acetate, methyl propionate, and butyl acetate; and aliphatic and cyclic ethers, such as dimethyl ether, tetrahydrofuran, and dioxane. If necessary, the miscibility of the desorbent with water and/or the organic compound may be facilitated by varying the temperature and/or using a co-solvent. Solvent pairs such as ethanol-cyclohexanone and tetrahydrofuran-methanol are examples of the use of a co-solvent to make the desorbent miscible with the aqueous feed solution containing the organic compound. If the desorbent is a mixture of solvents, the desorbent mixture may be fed into the SMB at single location or the individual solvent components of the desorbent may be fed at multiple locations.

In the present invention, the aqueous feed solution and the desorbent are fed into the SMB at at least 2 locations. If the desorbent is a mixture of solvents, then the aqueous feed solution, the desorbent, or the individual components of the desorbent may be fed into the SMB at more than 2 locations for operational convenience or to facilitate the adsorption/desorption phenomena occurring within the SMB. Typically, the volume ratio of the amount of desorbent fed to the SMB per volume of aqueous feed solution is in the range of about 1:1 to 10:1 with a volume ratio of 2:1 to 4:1 being more preferred.

The effluent from the SMB is removed in two or more liquid streams. Typically, there are two liquid streams: (i) a first liquid stream comprising the organic compound and the desorbent and (ii) a second liquid stream comprising water from the aqueous feed solution containing the organic compound. The first liquid stream comprises a the organic compound and the desorbent while the second liquid stream comprises water from the aqueous feed solution of the organic compound. The first and second effluent streams may comprise a mixture of the organic compound, water, and the desorbent. The desorbent may be the major (i.e., present at concentrations of greater than 50 wt %) component of the first liquid stream apart from the organic compound. Similarly, water may be the major component of the second liquid stream. According to one aspect of our novel process, the first liquid stream of the effluent has a water concentration of 50% or less, by weight, of the water concentration of the aqueous feed solution to the SMB. For example, if the aqueous feed solution contained 80 wt % water, the first liquid stream would contain 40 wt % or less water. In another example, the first liquid stream of the effluent has a water concentration of 20% or less, by weight, of the water concentration of the aqueous feed solution, and in yet another example, the concentration of water in the first liquid stream is 10% or less, by weight, of the aqueous feed solution.

Where the aqueous feed solution is the product of a fermentation process, the first and second liquid effluent streams also may comprise impurities from the fermentation process. These impurities may be removed in a third effluent stream from the SMB.

The SMB may be operated over a broad range of temperature and pressure. The temperature may be from about 30° C. to about 250° C. and is limited by the boiling point at the operating pressure of the materials fed to the SMB. Examples of temperature ranges that may be used are about 10 to about 150° C., about 40 to about 120° C., and about 50 to 90° C. Pressure is not a critical feature of the process. Thus, with the above ranges of temperature, pressures between about 330 to about 3500 kPa gauge may be used. Typically, the pressure range is between about 350 and 2000 kPa gauge.

The process of the present invention also provides a process for separating water from an organic compound comprising (I) feeding (i) an aqueous solution comprising at least one organic compound selected from alcohols, ethers, ketones, polyhydroxy compounds, and esters; and (ii) at least one desorbent selected from alcohols, ethers, ketones, and esters, having at least a partial solubility in water to a simulated moving bed comprising at least one solid having different adsorptivities for said organic compound and water; and (II) removing from said simulated moving bed (i) a first liquid stream comprising a solution of said organic compound in the desorbent and (ii) a second liquid stream comprising water from said aqueous solution of step I. The solid or adsorbents may include activated carbon, molecular sieves, alumina, silica, silica-alumina, titania, polymeric resins containing one or more groups selected from sulfonate, hydroxy, amino, halogen, pyridyl, monosubstituted amino, disubstituted amino, acyl, acyloxy, keto, alkoxy, and polymeric resins containing immobilized silver or lead. In one embodiment, the solid is a sulfonated polymeric resin, such as an acidic ion exchange resin, e.g., a macroreticulated polymeric material derived from styrene or styrene and divinylbenzene containing pendant sulfonic acid groups.

The aqueous solution comprises at least one organic compound selected from alcohols, polyhydroxy compounds, esters. The organic compound may contain from 1 to about 20 carbon atoms. The organic compound also may be a product from biomass extraction, or a biocatalytic, fermentation, or enzymatic process, such as, for example, an aqueous solution of a sugar. Examples of sugars which may be dewatered by our process include monosaccharides, such as including fructose (levulose), sorbose; glucose (dextrose), mannose, and galactose. Sugars may also include oligosaccharides, which are commonly understood in the art to mean simple polysaccharides containing a known number of constituent monosaccharide units. Examples of oligosaccharides are sucrose, maltose, and lactose. The organic compound may also be a carbohydrate such as starch, glycogen, cellulose and pentosans.

The organic compound also may be an ester of acetic acid, propionic acid, n-butyric acid, 2-butyric acid, or isobutyric acid. Examples of esters include, but are not limited to, methyl acetate, methyl propionate, ethyl acetate, butyl acetate, ethyl butyrate, 2-ethylhexylisobutyrate, 2-ethylhexyl-n-butyrate, propyl butyrate, propyl acetate, propyl proprionate, benzyl acetate, and benzyl butyrate. In addition, the organic compound may be an alcohol or polyhydroxy compound such as, but not limited to methanol, ethanol, propanol, isopropanol, 1-butyl alcohol, 2-butyl alcohol, isobutanol, 1-pentanol, 1,6-hexanediol, ethylene glycol, 1,2-propanediol, 1,3-propanediol, 1,2-butanediol, 1,3-butanediol, 1,4-butanediol, pentaerythritol, or trimethylolpropane.

As described hereinabove, the desorbent may be a single solvent or a mixture of solvents and may contain small amounts (10 wt % or less) of water. Example ranges of water concentrations that may be present in the desorbent are from about 0.5 to about 10 wt %, about 1 to about 8 wt %, and about 3 to about 5 wt %. Examples of desorbents include one or more alcohols, diols, esters, nitriles, ketones, and ethers an alcohol, e.g., a straight- or branched-chain, unsubstituted or substituted alcohol containing up to about 8 carbon atoms. Preferably, the desorbent is methanol, ethanol, or acetone. Although not critical, the simulated moving bed may be maintained at a temperature of 90 to 120° C. and a pressure of about 350 to 2000 kilopascals gauge to prevent boiling of the liquid components within the SMB. Two liquid effluent streams are removed from the SMB: (i) a first liquid stream comprising the organic compound and the desorbent and (ii) a second liquid stream comprising water from the aqueous feed solution of containing the organic compound. As described above, the first and second liquid streams may comprise a mixture of the organic compound, water, and the desorbent. The desorbent may be the major component (i.e., greater than 50% by weight) of the first liquid stream apart from the organic compound. In addition, water may be the major component of the second liquid stream. According to one aspect of our novel process, first liquid stream may a water concentration of 50% or less, by weight, of the water concentration of the aqueous feed solution to the SMB. In another example, the first liquid stream may have a water concentration of 20% or less, by weight, of the water concentration of the aqueous feed solution, and in yet another example, the concentration of water in the first liquid stream is 10% or less, by weight, of the aqueous feed solution. A third liquid effluent stream also may be removed from the SMB, if necessary, for the removal or separation of additional organic and inorganic impurities. This stream typically comprises an aqueous solution of organic and inorganic impurities and the desorbent.

The present invention is further described and illustrated by the following examples.

EXAMPLES

General

All percentages given in the examples are by weight unless specified otherwise. Pulse tests were conducted to determine the feasibility of separating water from an organic compound using an SMB. A SMB may be designed by those skilled in the art based on information obtained from pulse tests. The use of laboratory pulse tests to determine the key operating parameters and as a test to establish the utility of an SMB for a specific separation is well known in the art (see, for example S. R. Perrin, R. M. Nicoud, *Chiral Separation Techniques: A Practical Approach*, Wiley-VCH Verlag GmbH, Weinheim, 2001, Chapter 10, pp. 262–267). In general, a pulse test is conducted by packing a column with a solid that is capable of separating the different components in the feed mixture. The column is preconditioned by pumping a mobile phase, such as water or methanol, through the column. A pulse of the feed mixture is introduced into the column. This is followed by elution of the feed mixture by pumping the desorbent through the column. The effluent streams are analyzed and a chromatogram prepared by plotting the concentration of various components in the effluent fractions against the elution time or volume. A resolution of about 0.75 or greater between the elution peaks of the solute (i.e., the organic compound) and water indicates that separation of water and the solute can be accomplished using a SMB.

A pulse test system was constructed using a commercial high-pressure, liquid chromatography system (HP-1050 from Agilent, formerly Hewlett Packard) and a refractive index detector (available from Waters Corporation). The desorbent in all experiments was methanol. The temperature was controlled at 40 C for all experiments. The acidic, polysulfonated resin used in the experiments was a Rezex Fast Fruit® 8% H column (7.8×100 mm) with 8 mm particles (catalog number 00D-02230K0, available from Phenomenex). Immobilized metal affinity columns (IMAC) of similar dimensions were obtained from this source also. The refractive index detector output signal was collected by a analog-to-digital (A-D) converter and digitized at 5 Hz. This signal was processed by the Turbochrom® software suite (available from Perkin Elmer Company).

Water was detected by monitoring changes in refractive index (RI) of the column effluent passed through a sample cell in comparison to a reference cell filled with the desorbent. Prior to the dewatering experiments, the refractive index detector was primed with methanol and the detector response was set to "0". The presence of water or solute in the column effluent causes a positive response from the RI detector. In addition to the RI detection system, the identity the peaks eluting from the column were verified by comparision to known compounds.

Examples 1–11

Dewatering Organic Compounds with an Acidic Polysulfonated Resin. A series of organic compounds (referred to herein as "solutes") were selected to demonstrate the dewatering process using an acidic, polysulfonated resin. In all cases the solute was exchanged from an aqueous solvent into the desorbent (in these examples, methanol). The results of the dewatering experiments are provided in Table 1.

TABLE 1

Dewatering Experiments Using an Acidic, Polysulfonated Resin

| Example | Solute | Desobent | Resolution |
|---|---|---|---|
| 1 | Glucose | Methanol | Greater than 1.0 |
| 2 | Xylose | Methanol | Greater than 1.0 |
| 3 | Maltose | Methanol | Greater than 1.0 |
| 4 | Acetone | Methanol | Greater than 1.0 |
| 5 | Butanol | Methanol | Greater than 1.0 |
| 6 | Xylitol | Methanol | Greater than 1.0 |
| 7 | Sorbitol | Methanol | Greater than 1.0 |
| 8 | 1,2-Propanediol | Methanol | Greater than 1.0 |
| 9 | Ethanol | Methanol | Greater than 1.0 |
| 10 | KLG | Methanol | Greater than 1.0 |
| 11 | Acetic Acid | Methanol | Greater than 1.0 |

Examples 12–22

Dewatering test solutes using IMAC columns. A second study was conducted using methanol desorbent and the same solutes as in Examples 1–11, but using a a Pb-based immobilized metal affinity column (IMAC) as the stationary phase. In this system, several of the solutes (Examples 12, 13, 14, 17, 18, and 21; see Table 2) were strongly adsorbed onto the stationary phase and did not elute under conditions of the experiment; however, the remaing solutes did elute from the column and showed resolutions comparable to Examples 1–11 with the exception of 1,2-propanediol. The results are presented in Table 2.

TABLE 2

Dewatering Experiments Using IMAC (Pb+) Resin

| Example | Solute | Desorbent | Resolution |
|---|---|---|---|
| 12 | Glucose | Methanol | Greater than 1.5 |
| 13 | Xylose | Methanol | Greater than 1.5 |
| 14 | Maltose | Methanol | Greater than 1.5 |
| 15 | Acetone | Methanol | Greater than 0.5 |
| 16 | Butanol | Methanol | Greater than 0.5 |
| 17 | Xylitol | Methanol | Greater than 1.5 |
| 18 | Sorbitol | Methanol | Greater than 1.5 |
| 19 | 1,2-Propanediol | Methanol | Between 0.5–0.75 |
| 20 | Ethanol | Methanol | Greater than 1.0 |
| 21 | KLG | Methanol | Greater than 1.5 |
| 22 | Acetic Acid | Methanol | Greater than 1.0 |

We claim:

1. A process for separating water from an organic compound comprising:
    I. feeding (i) an aqueous solution comprising at least one organic compound which is not a carboxylic acid and (ii) at least one desorbent, other than water, having at least a partial solubility in water to a simulated moving bed comprising at least one solid having different adsorptivities for said organic compound and water; and
    II. removing from said simulated moving bed (i) a first liquid stream comprising said organic compound and said desorbent and (ii) a second liquid stream comprising water from said aqueous solution of step I.

2. The process according to claim 1 in which said simulated moving bed contains from 4 to 20 sections.

3. The process according to claim 2 in which said solid is selected from activated carbon; molecular sieves; alumina; silica; silica-alumina; titania; polymeric resins containing one or more groups selected from sulfonate, hydroxy, amino, halogen, pyridyl, mono-substituted amino, disubstituted amino, acyl, acyloxy, keto, and alkoxy; and polymeric resins containing immobilized silver or lead.

4. The process according to claim 3 in which said solid is a sulfonated polymeric resin.

5. The process according to claim 4 which said organic compound is selected from alcohols, sugars, polyhydroxy compounds, esters, carbohydrates, aldehydes, sulfones, thioketones, oximes, ketones, nitrites, amides, lactones, lactams, phenols, amines, ethers, and $C_4$ to $C_{10}$ heterocyclic compounds containing from 1 to 3 heteroatoms.

6. The process according to claim 5 in which said desorbent comprises at least one solvent selected from alcohols, diols, esters, nitriles, ketones, and ethers.

7. The process according to claim 6 in which said first liquid stream of step II has a water concentration of 50% or less, by weight, of the water concentration of the aqueous solution of step I.

8. The process according to claim 7 in which said first liquid stream of step II has a water concentration of 20% or less, by weight, of the water concentration of the aqueous solution of step I.

9. The process according to claim 8 in which said simulated moving bed is maintained at a temperature of about 10 to 150° C. and a pressure of about 330 to 3500 kPa gauge.

10. The process according to claim 9 in which said simulated moving bed is maintained at a temperature of about 50 to 90° C.

11. A process for separating water from an organic compound comprising:
   I. feeding (i) an aqueous solution comprising at least one organic compound selected from alcohols, ethers, ketones, polyhydroxy compounds, and esters; and (ii) at least one desorbent selected from alcohols, esters, ketones, and ethers, having at least a partial solubility in water to a simulated moving bed comprising at least one solid having different adsorptivities for said organic compound and water; and
   II. removing from said simulated moving bed (i) a first liquid stream comprising said organic compound and said desorbent and (ii) a second liquid stream comprising water from said aqueous solution of step I.

12. The process according to claim 11 in which said solid is an sulfonated polymeric resin.

13. The process according to claim 12 in which said organic compound contains from 1 to about 20 carbon atoms.

14. The process according to claim 13 in which said organic compound is a product from a fermentation or enzymatic process.

15. The process according to claim 13 in which said organic compound is a sugar.

16. The process according to claim 15 in which said organic compound is glucose, fructose, sucrose, maltose, or mixtures thereof.

17. The process according to claim 13 in which said organic compound is an ester of acetic acid, propionic acid, n-butyric acid, 2-butyric acid, or isobutyric acid.

18. The process according to claim 13 in which said organic compound is ethylene glycol, 1,2-propanediol, 1,3-propanediol, 1,2-butanediol, 1,3-butanediol, 1,4-butanediol, pentaerythritol, or trimethylolpropane.

19. Process according to claim 13 in which the desorbent is methanol, ethanol, or acetone and the simulated moving bed is maintained at a temperature of 90 to 120° C. and a pressure of about 350 to 2000 kilopascals gauge.

20. The process according to claim 19 in which said first liquid stream of Step II has a water concentration of 50% or less, by weight, of the water concentration of the aqueous solution of Step I.

21. The process according to claim 20 in which said first liquid stream of Step II has a water concentration of 20% or less, by weight, of the water concentration of the aqueous solution of Step I.

* * * * *

UNITED STATES PATENT AND TRADEMARK OFFICE
CERTIFICATE OF CORRECTION

PATENT NO. : 6,872,314 B2
DATED : March 29, 2005
INVENTOR(S) : Boyd et al.

It is certified that error appears in the above-identified patent and that said Letters Patent is hereby corrected as shown below:

Column 13,
Line 13, reads "thioketones, oximes, ketones, nitrites, amides, lactones," should read
-- thioketones, oximes, ketones, nitriles, amides, lactones, --

Signed and Sealed this

Seventh Day of June, 2005

JON W. DUDAS
*Director of the United States Patent and Trademark Office*